United States Patent [19]

Baker

[11] Patent Number: 4,874,753

[45] Date of Patent: Oct. 17, 1989

[54] INSECTICIDAL COMPOSITION

[75] Inventor: Rodney C. Baker, Berkhamsted, England

[73] Assignee: AECI Limited, Johannesburg, South Africa

[21] Appl. No.: 801,306

[22] Filed: Nov. 25, 1985

[51] Int. Cl.$^4$ .................. A01N 37/34; A01N 43/38; A01N 53/00; A01N 57/00

[52] U.S. Cl. .................................... 514/89; 514/80; 514/86; 514/136; 514/421; 514/521; 514/531

[58] Field of Search ........................... 514/89

[56] References Cited

U.S. PATENT DOCUMENTS

| | | | |
|---|---|---|---|
| 4,018,932 | 4/1977 | Spicer et al. | 514/368 |
| 4,171,355 | 10/1979 | Stubbs et al. | 514/89 |

FOREIGN PATENT DOCUMENTS

| | | |
|---|---|---|
| 77/1003 | 2/1977 | South Africa . |
| 77/7609 | 12/1977 | South Africa . |
| 81/5273 | 7/1981 | South Africa . |
| 81/6661 | 9/1981 | South Africa . |
| 81/8079 | 11/1981 | South Africa . |
| 82/7614 | 10/1982 | South Africa . |
| 83/3066 | 4/1983 | South Africa . |
| 84/8150 | 10/1984 | South Africa . |
| 1488906 | 10/1977 | United Kingdom . |

*Primary Examiner*—Douglas K. Robinson
*Attorney, Agent, or Firm*—Cushman, Darby & Cushman

[57] ABSTRACT

A pour-on formulation for localized external application to dogs includes an effective amount of a non-systemic insecticide which is tolerated by dogs and which is effective against fleas and/or ticks. It also includes a $C_1$–$C_4$ alcohol as carrier for the insecticide. The formulation contains no pyrethroid, no spreading oil and no gel- or film forming agent.

9 Claims, No Drawings

INSECTICIDAL COMPOSITION

This invention relates to pour-on formulations.

According to a first aspect of the invention, there is provided a pour-on formulation for localized external application to dogs, which includes an effective amount of a non-systemic insecticide which is tolerated by dogs and which is effective against fleas and/or ticks; and a $C_1$–$C_4$ alcohol as carrier for the insecticide, with the proviso that the formulation contains no pyrethroid, no spreading oil and no gel or filmforming agent.

By 'non-systemic insecticide' is meant an insecticide which does not act to any appreciable extent by transmission through the bloodstream of the animal. Hence, when a non-systemic insecticide is applied externally to the pelt of the animal, the insecticide does not penetrate the pelt or skin of the animal to a significant degree. The composition will also not contain additives which cause the insecticide to penetrate significantly into the skin.

The composition will either be in the form of a solution or in the form of a dispersion of fine insecticide particles in the carrier, depending on the insecticide and the alcohol.

Typically, pour-on formulations are applied to a minor portion of the outer surface of an animal's skin or pelt, generally in a line along the animal's back. From there, the insecticide migrates to protect substantially the whole outer surface of the animal's skin or pelt.

By 'spreading oil' is meant an oil-based liquid which spreads readily on the skin or pelt of the dog, such as silicone oils; fatty alcohols, acids or acid esters' triglycerides, etc. Such spreading oils are well known as such in the cosmetics industry.

The formulation may include from 1 to 10% (m/v), ie 1 to 10 grams/100 ml, of the insecticide, and at least 90% by volume of the alcohol. It may contain at least 92% by volume alcohol, eg 92% to 96% by volume alcohol. It may include from 5% to 8% (m/v) of the insecticide.

The insecticide may comprise at least of the following:

amitraz (ie N,N-di-(2,4-xylyliminomethyl) methylamine or 1,5-di(2-4-dimethyl-phenyl)-3-methyl-1,3,5-triazapenta-1,4-diene);

lindane (ie 1,2,3,4,5,6-hexachlorocyclohexane);

diazinon (ie 0,0-diethyl-0-(2-isopropyl-6-methyl pyrimidine-4-yl)phosphorothioate);

propoxur (ie 2-isopropoxyphenyl methylcarbamate);

tetrachlorvinphos (ie 2-chloro-1-(2,4,5-trichloro-phenyl) vinyl dimethyl phosphate);

dursban (ie 0,0-diethyl-0-(3,5,6-trichloro-2-pyridyl)-phosphorothioate);

carbaryl (ie 1-naphthalenyl methyl carbamate);

phosmet (0,0-dimethyl S-phthalimidomethyl phosphorodithioate) which may be in recrystallized from for removal or reduction its offensive odour.

In particular, the insecticide may comprise an organophosphorus compound. The organophosphorus compound may be dursban. The alcohol may be a straight chain alcohol. In particular, it may be an aliphatic alcohol, and more particularly, it may be a monohydric alcohol.

The formulation may also contain from 0.05 to 5% (m/v) of one or more chemical stabilizers such as epichlorohydrin, epoxidized linseed oil, epoxidized soya bean oil, or the like.

The formulation may further include a masking agent to mask the odour of the residual insecticide on the animal.

The formalution may be in unit dosage form, for example, it may be contained in sealed container of a material which is inert to the carrier. To use the formulation the container is then merely opened (eg punctured) and the formulation applied along the back of the animal.

According to a second aspect of the invention, there is provided a method of making a pour-on formulation for localized external application to dogs, which includes admixing an effective amount of a non-systemic insecticide which is tolerated by dogs and which is effective against fleas, and a $C_1$–$C_4$ alcohol, with the proviso that no pyrethroid, no spreading oil and no gel- or film-forming agent are added to the admixture.

According to a third aspect of the invention, there is provided a method of controlling ticks and/or fleas on a dog, which includes making, on a dog, localized external applications several times a year of a pour-on formulation comprising an effective amount of non-systemic insecticide which is tolerated by dogs and which is effective against ticks and/or fleas; and a $C_1$–$C_4$ alcohol as carrier for the insecticide.

The applications may be effected at regular intervals, and may be effected by pouring the formulation onto the back of the animal. The applications may be effected at intervals of 1–4 weeks, for example about 2–3 weeks. However, if desired, the applications can be effected at intervals of more than 4 weeks.

The formulation may include from 1 to 10% (m/v) of the insecticide, at least 90% (by volume) of the carrier, and substantially no spreading oil and gel- or film-forming agent. As mentioned hereinbefore, the insecticide may comprise an organophosphorus compound and the carrier may be a monohydric aliphatic alcohol.

The formulation may include a further non-systemic insecticide. The further insecticide may comprise a synthetic pyrethroid optionally admixed with a synergist, such as piperonyl butoxide.

The synthetic pyrethroids may comprise permethrin (ie 3-phenoxybenzyl -(±)-cis, trans-2,2-dimethyl-3-(2,2-dichlorovinyl) cyclopropane-1-carboxylate); and/or decamethrin/deltamethrin (ie S-α-cyano-3-phenoxy benzyl-(1R,3R)2,2-dimethyl-3-9(,2-dibromovinyl) cyclopropane-1 carboxylate); and/or tetramethrin (ie 3,4,5,6.tetrahydro-phthalimidomethyl(±)cis,transchrysanthemate); and/or cypermethrin (ie -cyano-3-phenoxybenyzyl-3-(2,2-dichlorovinyl)-2,2-dimethylcyclopropane-carboxylate); and/or flumethrin (ie -cyano-3-phenoxy-4-fluoro-benzyl-3-(2-chloro-2-(4-chlorophenyl)vinyl)2,2-dimethylcyclopropane carboxylate.

More particularly, the formulation may comprise a mixture of dursban and permethrin as the insecticide, and n-propanol as the carrier. In particular, the formulation may include about 4%(m/v) dursban and about 4%(m/v) permethrin, the balance to make up 100 volume units being n-propanol.

The invention will now be described by way of example with reference to the following non-limiting Examples: ting Examples:

EXAMPLE 1

The follwing constituents were admixed to form a pour-on insecticidal formulation suitable for use on dogs:

| dursban active (optionally deoderized) | 4% (m/v) or | 5,16% (m/m) |
| permethrin | 4% (m/v) or | 4,84% (m/m) |
| n-propanol as carrier (balance to make up 100 ml of composition). | 75% (m/v) or | 90,00% (m/m) |

EXAMPLE 2

The following constituents were admixed to form a pour-on insecticidal formulation suitable for use on dogs:

| dursban (chlorpyrifos) | 4,0% m/v |
| associated impurities | 0,04% m/v |
| n-propanol | balance to make up 100 ml of composition. |

The insecticidal formulations of the Examples can be applied to dogs at a rate of about 30 to about 60 mg insecticide per kilogram mass of animal, ie 15 to 30 mg/kg each of dursban and permethrin in the case of the formulation of Example 1. For example, the Applicant envisages that the formulations of the Examples will be applied to dogs at the following rates:

| large dogs (ie 20–40 kg mass) - 30 ml of composition; |
| medium dogs (ie 10–20 kg mass) - 15 ml of composition; |
| small dogs (ie 5–10 kg mass) - 7½ ml of composition. |

This should provide a sufficient volume of the pour-on solution to pour in a line along the back of the dog.

The formulations of the Examples are preferably provided in unit dosage form, and may be provided in air-tight containers such as tubes (eg of aluminium), bottles (eg of glass) or the like, of a desired capacity. The containers may be such that, on being opened (eg punctured), the flow of the formulation composition therefrom is restricted (eg by having a suitably sized nozzle or orifice) thereby to enable the formalation or composition to be poured along substantially the entire length of the dog's back.

The alcohol evaporates readily after application, and hence only the substantially non-greasy or non-oily insecticide adheres to the pelt or skin of the animal. Furthermore, there is little or no run-off of insecticide.

The Applicant is aware of liquid insecticidal formulations or compositions which are applied to the skins of animals, eg for control of ticks on the animals. These compositions include a systemic insecticide and a liquid carrier, such as a spreading oil, for the insecticide. However, these compositions have the drawback that they, on application to the skin of the animal, penetrate through the tissues of the animal into its bloodstream where the insecticide is often broken down, thereby reducing its efficacy. Furthermore, an oil deposit remains on the pelt of the animal after application. When the animal is a household pet, this oily deposit is unsightly and can easily rub off onto a person handling the animal.

The Applicant is also aware of a pour-on formulation for cattle comprising a non-systemic insecticide and a spreading oil. However, this composition also gives rise to an oily deposit as described hereinbefore.

The Applicant is also aware that insecticides have hitherto been applied to dogs by washing the animals with a soap, dip or shampoo containing an insecticide. However, it is laborious and time consuming to wash the animal with such a soap, dip or shampoo.

The Applicant is further aware that insecticides have hitherto also been applied to dogs by fitting an insecticide-containing collar to the animal. However, such a collar is prone to being damaged or lost while being worn by the animal.

The Applicant believes that these drawbacks are at least partially reduced with the formulations of the present invention. The Applicant also believes that the insecticidal formulations of the present invention provides a means by which an insecticide can be applied to a dog easily and safely. The pour-on composition of the present invention are also easy to make. The Applicant still further believes that the insecticidal formulations of the invention will be effective in reducing not only fleas on dogs, but also ticks.

Biological trials were conducted under controlled conditions, and the results are set out in Tables 1 to 10.

TABLE 1

TICK COUNTS ON DOGS TREATED WITH THE COMPOSITIONS OF EXAMPLES 1 AND 2 UNDER CONTROLLED TRIAL CONDITIONS

| | Composition of EXAMPLE 2 | | | Composition of EXAMPLE 1 | | | Untreated Control |
|---|---|---|---|---|---|---|---|
| DAY | DOG A | DOG B | AV | DOG C | DOG D | AV | DOG E |
| −2 | | | | TICK CHALLENGE | | | |
| 0 | 15(19) | 8(26) | 34 | 24(12) | 16(11) | 32 | 30(29) |
| 0 | | | | DOGS TREATED | | | |
| 1 | 9(6) | 9(3) | 14 | 6 (1) | 6(0) | 7 | 30(29) |
| 4 | 8(0) | 4(1) | 7 | 3 (4) | 4(2) | 7 | 26(30) |
| 5 | | | | TICK CHALLENGE | | | |
| 8 | 7(0) | 3(1) | 6 | 1(0) | 2(0) | 2 | 27(21) |
| 11 | 6(0) | 2(0) | 4 | 0 | 0(1) | 1 | 33(28) |
| 12 | | | | TICK CHALLENGE | | | |
| 15 | 7(0) | 6(2) | 8 | 0 | 0 | 0 | 28(34) |
| 18 | 4(1) | 4(1) | 5 | 0 | 0 | 0 | 22(24) |
| 19 | | | | TICK CHALLENGE | | | |
| 22 | 5(3) | 14(10) | 16 | 0 | 0 | 0 | 22(28) |
| 25 | 7(2) | 4(6) | 10 | 0 | 0 | 0 | 23(27) |
| 26 | | | | TICK CHALLENGE | | | |
| 29 | 4(9) | 6(11) | 15 | 1(0) | 0 | 1 | 12(23) |

TABLE 1-continued

TICK COUNTS ON DOGS TREATED WITH THE COMPOSITIONS OF EXAMPLES 1 AND 2 UNDER CONTROLLED TRIAL CONDITIONS

| DAY | Composition of EXAMPLE 2 | | | Composition of EXAMPLE 1 | | | Untreated Control |
|---|---|---|---|---|---|---|---|
| | DOG A | DOG B | AV | DOG C | DOG D | AV | DOG E |
| 32 | 1(9) | 3(14) | 14 | 1(0) | 0 | 1 | 10(28) |
| 33 | | | | TICK CHALLENGE | | | |
| 39 | | | | 0 | 5(1) | 3 | 24(27) |
| 40 | | | | TICK CHALLENGE | | | |
| 43 | | | | 1(0) | 6(0) | 4 | 26(22) |
| 46 | | | | 0 | 3(0) | 2 | 27(22) |
| 47 | | | | TICK CHALLENGE | | | |
| 49 | | | | 2(2) | 5(9) | 9 | 30(22) |
| 53 | | | | 3(1) | 5(9) | 9 | 27(24) |
| 54 | | | | TICK CHALLENGE | | | |
| 57 | | | | 2(1) | 12(15) | 15 | 35(17) |
| 60 | | | | 2(1) | 12(10) | 13 | 35(19) |
| 61 | | | | TICK CHALLLNGE | | | |
| 63 | | | | 5(3) | 16(17) | 21 | 39(17) |
| 68 | | | | 9(4) | 17(11) | 21 | 29(13) |

Legend
(i) a(b): a represents *Haemaphysalis leachi* ticks
b represents *Rhipicephalus sanguineus* ticks
(ii) AV: Average
(iii) TICK CHALLENGE: 40 *Haemaphysalis leachi* ticks and 40 Rhipicephalus sanguIneus ticks introduced onto each dog.
(iv) DOGS TREATED: The compositions were applied to each dog at a rate of 30 mg total insecticide per kilogram body mass.

TABLE 2

FLEA COUNTS ON DOGS TREATED WITH THE COMPOSITIONS OF EXAMPLES 1 AND 2 UNDER CONTROLLED TRIAL CONDITIONS

| DAY | Composition of EXAMPLE 2 | | | Composition of EXAMPLE 1 | | | Untreated Control |
|---|---|---|---|---|---|---|---|
| | DOG A | DOG B | AV | DOG C | DOG D | AV | DOG E |
| −2 | | | | FLEA CHALLENGE | | | |
| 0 | 58 | 20 | 39 | 36 | 21 | 29 | 68 |
| 0 | | | | DOGS TREATED | | | |
| 1 | 0 | 0 | 0 | 0 | 0 | 0 | 68 |
| 4 | 0 | 0 | 0 | 0 | 0 | 0 | 50 |
| 5 | | | | FLEA CHALLENGE | | | |
| 8 | 0 | 0 | 0 | 0 | 0 | 0 | 62 |
| 11 | 0 | 0 | 0 | 0 | 0 | 0 | 50 |
| 12 | | | | FLEA CHALLENGE | | | |
| 15 | 0 | 0 | 0 | 0 | 0 | 0 | 66 |
| 18 | 0 | 0 | 0 | 0 | 0 | 0 | 62 |
| 19 | | | | FLEA CHALLENGE | | | |
| 22 | 1 | 1 | 1 | 4 | 2 | 2 | 65 |
| 25 | 0 | 2 | 1 | 3 | 0 | 2 | 54 |
| 26 | | | | FLEA CHALLENGE | | | |
| 29 | 10 | 22 | 16 | 10 | 6 | 8 | 56 |
| 32 | 10 | 20 | 15 | 9 | 1 | 5 | 59 |
| 33 | | | | FLEA CHALLENGE | | | |
| 39 | | | | 17 | 8 | 13 | 56 |
| 40 | | | | FLEA CHALLENGE | | | |
| 43 | | | | 33 | 23 | 28 | 67 |
| 46 | | | | 25 | 23 | 24 | 62 |

Legend
(i) AV: Average
(ii) FLEA CHALLENGE: 100 *Ctenecephalides: felis* fleas were introduced onto each dog.
(iii) DOGS TREATED: As for Table 1

TABLE 3

TICK COUNT ON FIELD DOGS TREATED WITH THE COMPOSITIONS OF EXAMPLES 1 AND 2

| | Composition of EXAMPLE 2 | | Composition of EXAMPLE 1 | | | |
|---|---|---|---|---|---|---|
| | SHORT HAIR | LONG HAIR | SHORT HAIR | | | LONG HAIR |
| DAY | DOG E | DOG G | DOG H | DOG I | DOG J | DOG K |
| −2 | — | 14 | — | — | — | 9 |
| 0 | 47 | 15 | 4 | 4 | 16 | 9 |
| 0 | | | DOGS TREATED | | | |

TABLE 3-continued

TICK COUNT ON FIELD DOGS TREATED WITH THE COMPOSITIONS OF EXAMPLES 1 AND 2

| | Composition of EXAMPLE 2 | | Composition of EXAMPLE 1 | | | |
| --- | --- | --- | --- | --- | --- | --- |
| | SHORT HAIR | LONG HAIR | SHORT HAIR | | | LONG HAIR |
| DAY | DOG E | DOG G | DOG H | DOG I | DOG J | DOG K |
| 1 | 19 | 8 | 0 | 1 | 10 | 7 |
| 4 | 21 | 4 | 0 | 0 | 10 | 1 |
| 7 | 19 | 3 | 0 | 0 | 6 | 1 |
| 11 | 26 | 6 | 0 | 0 | 3 | 2 |
| 14 | 39 | 4 | 1 | 0 | 0 | 1 |
| 18 | 39 | 8 | 1 | 0 | 1 | 1 |
| 20 | 49 | 8 | 1 | 0 | 6 | 0 |
| 20/0 | RETREATED | | | RETREATED | | |
| 21/1 | 35 | — | — | 0 | 0 | — |
| 25/5 | 11 | 2 | 1 | 0 | 0 | 2 |
| 28/8 | 14 | 3 | 0 | 2 | 0 | 0 |
| 35/15 | 20 | — | 0 | 1 | 0 | — |
| 42/23 | 25 | — | — | 2 | 1 | — |

Legend
(i) —: No Count
(ii) DOGS TREATED: As for Table 1
(iii) RETREATED: As for dogs treated

TABLE 4

FLEA COUNTS ON FIELD DOGS TREATED WITH THE COMPOSITIONS OF EXAMPLES 1 AND 2

| | Composition of EXAMPLE 2 | | | | | Composition of EXAMPLE 1 | | | | | | | |
| --- | --- | --- | --- | --- | --- | --- | --- | --- | --- | --- | --- | --- | --- |
| | SHORT HAIR | | | | | SHORT HAIR | | | | LONG HAIR | | | |
| | Dog L | Dog M | Dog N | Dog I | Dog P | Dog Q | Dog R | Dog S | Dog T | Dog U | Dog V | Dog W | Dog X | Dog Y |
| −2 | — | — | — | — | 11 | — | — | — | — | — | 15 | — | — | — |
| 0 | 100 | 22 | 40 | 14 | 12 | 22 | 30 | 90 | 300 | 11 | 13 | 29 | 11 | 20 |
| 0 | | | | | | DOGS TREATED | | | | | | | | |
| 1 | 8 | 8 | 9 | 7 | 1 | 10 | 0 | 10 | 0 | 1 | 0 | 4 | 1 | 0 |
| 4 | 4 | 11 | 3 | 1 | 1 | 2 | 0 | 6 | 2 | 3 | 0 | 1 | 0 | 2 |
| 7 | 7 | 7 | 2 | 1 | 0 | 2 | 0 | 5 | 2 | 1 | 0 | 0 | 0 | 1 |
| 11 | 11 | 6 | 3 | 0 | 2 | 1 | — | 21 | 5 | — | 2 | 4 | 1 | 5 |
| 14 | 13 | 2 | 2 | 1 | 1 | 0 | 4 | 40 | 50 | 9 | 5 | 6 | 3 | 9 |
| 18 | 13 | 3 | 7 | 4 | 1 | 4 | 5 | 44 | 75 | 6 | 4 | 4 | 10 | 7 |
| 20 | 29 | 13 | 4 | 2 | 4 | 13 | 4 | 43 | 130 | 5 | 7 | 12 | — | — |
| 0 | RETREATED | | | | | | | RETREATED | | | | | | |
| 1 | 1 | — | — | — | — | — | — | 6 | 1 | — | — | — | — | — |
| 35/5 | 1 | 11 | 15 | 10 | 5 | 17 | 2 | 14 | 4 | 6 | 4 | 12 | — | — |
| 33/8 | 0 | 14 | 19 | 10 | 5 | 10 | 3 | 14 | 9 | 6 | 6 | 9 | — | — |
| 32/12 | — | 16 | 35 | 12 | — | 16 | — | — | — | — | — | — | — | — |
| 35/15 | — | — | — | — | — | — | 1 | 11 | 15 | 4 | — | 1 | — | — |
| 42/23 | 1 | — | — | — | — | 7 | — | 32 | 96 | — | — | — | — | — |

Legend
(i) —: No count
(ii) DOGS TREATED: As for Table 1
(iii) RETREATED: As for Table 1

TABLE 5

TICK COUNTS ON DOGS TREATED WITH THE COMPOSITION OF EXAMPLE 1

| | Composition of EXAMPLE 1 | | | | | | | | | Untreated Controls | | |
| --- | --- | --- | --- | --- | --- | --- | --- | --- | --- | --- | --- | --- |
| | DOGS | | | | | | | | | DOGS | | |
| DAY | AA | BB | CC | DD | EE | FF | GG | HH | AV | JJ | KK | AV |
| −9 | | | | | | | TICK CHALLENGE | | | | | |
| −3 | 18(20) | 35(29) | 11(13) | B(10) | 11(16) | 14(21) | 11(13) | B(18) | 32 | 14(15) | 9(11) | 25 |
| −2 | | | | | | | TICK CHALLENGE | | | | | |
| 0 | 22(10) | 29(25) | 17(6) | 23(5) | 11(18) | 20(33) | 17(10) | 19(15) | 36 | 17(11) | 29(17) | 37 |
| 0 | | | | | DOGS TREATED | | | | | | | |
| 7 | 6(3) | 7(5) | 0(3) | 4(5) | 4(1) | 11(9) | 6(1) | 4(2) | 9 | 8(8) | 7(11) | 17 |
| 4 | 2(0) | 4(1) | 3(2) | 1(1) | 7(1) | 1(1) | 2(2) | 1(0) | 5 | 15(7) | 16(26) | 32 |
| 5 | | | | | | | TICK CHALLENGE | | | | | |
| 11 | 0 | 2(0) | 2(1) | 0 | 0 | 0 | 3(1) | 1(0) | 1 | 12(9) | 16(17) | 27 |
| 12 | | | | | | | TICK CHALLENGE | | | | | |
| 14 | 2(0) | 1(0) | 3(1) | 0 | 0(1) | 3(1) | 3(0) | 1(0) | 2 | 14(15) | 21(9) | 30 |
| 18 | 1(0) | 0(1) | 1(0) | 0 | 0(1) | 0(1) | 3(0) | 1(0) | 1 | 13(15) | 13(10) | 26 |
| 19 | | | | | | | TICK CHALLENGE | | | | | |

TABLE 5-continued
TICK COUNTS ON DOGS TREATED WITH THE COMPOSITION OF EXAMPLE 1

| | Composition of EXAMPLE 1 | | | | | | | | | Untreated Controls | | |
|---|---|---|---|---|---|---|---|---|---|---|---|---|
| | DOGS | | | | | | | | | DOGS | | |
| DAY | AA | BB | CC | DD | EE | FF | GG | HH | AV | JJ | KK | AV |
| 21 | 1(0) | 0 | 2(0) | 0 | 0 | 0(1) | 0 | 0 | 1 | 14(11) | 20(14) | 30 |
| 25 | 0 | 0(1) | 2(0) | 0 | 0 | 0(1) | 0 | 0 | 1 | 14(17) | 13(11) | 28 |
| 26 | | | | | TICK CHALLENGE | | | | | | | |
| 28 | 0(1) | 5(3) | 2(0) | 0 | 1(0) | 3(1) | 0 | 1(0) | 2 | 22(11) | 14(19) | 33 |
| 0 | | | | DOGS RETREATED | | | | | | | | |
| 3 | 0(1) | 2(0) | | | 0 | 0(1) | | | 1 | 19(12) | 16(17) | 32 |
| 4 | | | TICK CHALLENGE | | | | | | | | | |
| 6 | 0(1) | 2(0) | | | 0 | 2(1) | | | 1 | 17(12) | 14(13) | 28 |
| 10 | 0(1) | 3(0) | | | 0 | 1(0) | 1 | | 15(13) | 17(20) | 33 | |
| 11 | | | TICK CHALLENGE | | | | | | | | | |
| 13 | 0 | 2(1) | | | 0 | 3(0) | | | 2 | 15(15) | 22(13) | 33 |
| 17 | 0 | 5(0) | | | 0 | 4(0) | 2 | | 19(6) | 21(17) | 32 | |
| 18 | | | TICK CHALLENGE | | | | | | | | | |
| 20 | 2(0) | 4(0) | | | 0 | 3(3) | | | 3 | 22(10) | 18(19) | 35 |
| 24 | 1(0) | 5(1) | | | 0 | 7(5) | | | 5 | 18(8) | 15(23) | 32 |
| 25 | | | TICK CHALLENGE | | | | | | | | | |
| 26 | 1(0) | 9(1) | | | 0 | 10(2) | | | 6 | 21(10) | 27(10) | 34 |

Legend
(i) a(b): a represents *Haemaphysalis leachi* ticks b represents *Rhipicephalus sanguineus* ticks
(ii) AV: Average
(iii) DOGS TREATED: As for Table 1
(iv) TICK CHALLENGE: As for Table 1

TABLE 6
FLEA COUNTS ON DOGS TREATED WITH THE COMPOSITION OF EXAMPLE 1

| | Composition of EXAMPLE 1 | | | | | | | | Untreated Controls | | |
|---|---|---|---|---|---|---|---|---|---|---|---|
| | DOGS | | | | | | | | DOGS | | |
| DAY | AA | BB | CC | EE | FF | GG | HH | AV | JJ | KK | AV |
| −9 | | | | | | | FLEA CHALLENGE | | | | |
| −3 | 44 | 62 | 42 | 68 | 30 | 45 | 23 | 27 | 43 | 25 | 35 | 30 |
| −2 | | | | | | | FLEA CHALLENGE | | | | |
| 0 | 59 | 60 | 65 | 69 | 46 | 66 | 56 | 43 | 59 | 42 | 51 | 47 |
| 0 | | | | DOGS TREATED | | | | | | | |
| 1 | 0 | 0 | 9 | 1 | 2 | 1 | 1 | 0 | 2 | 47 | 54 | 51 |
| 4 | 0 | 0 | 0 | 0 | 0 | 0 | 0 | 0 | 0 | 34 | 48 | 41 |
| 5 | | | | | | | FLEA CHALLENGE | | | | |
| 11 | 1 | 0 | 0 | 0 | 0 | 0 | 0 | 0 | 0 | 37 | 48 | 43 |
| 12 | | | | | | | FLEA CHALLENGE | | | | |
| 14 | 0 | 0 | 1 | 0 | 0 | 0 | 6 | 0 | 1 | 52 | 59 | 56 |
| 18 | 0 | 0 | 0 | 0 | 0 | 0 | 0 | 0 | 0 | 35 | 39 | 37 |
| 19 | | | | | | | FLEA CHALLENGE | | | | |
| 21 | 3 | 13 | 1 | 1 | 0 | 16 | 1 | 0 | 4 | 53 | 46 | 50 |
| 25 | 1 | 14 | 1 | 2 | 0 | 9 | 4 | 0 | 4 | 50 | 44 | 47 |
| 26 | | | | | | | FLEA CHALLENGE | | | | |
| 28 | 16 | 33 | 3 | 11 | 8 | 16 | 6 | 0 | 12 | 51 | 50 | 51 |
| 0 | | | | DOGS RETREATED | | | | | | | |
| 3 | 0 | 0 | | 0 | 0 | | | 0 | 48 | 40 | 44 | |
| 4 | | | FLEA CHALLENGE | | | | | | | | | |
| 6 | 0 | 0 | | 0 | 0 | | | 0 | 52 | 60 | 56 | |
| 10 | 0 | 0 | | 0 | 0 | | | 0 | 43 | 29 | 36 | |
| 11 | | | FLEA CHALLENGE | | | | | | | | | |
| 13 | 0 | 0 | | 0 | 0 | | | 0 | 49 | 47 | 48 | |
| 17 | 0 | 0 | | 0 | 0 | | | 0 | 44 | 44 | 44 | |
| 15 | | | FLEA CHALLENGE | | | | | | | | | |
| 20 | 1 | 5 | | 0 | 2 | | | 2 | 46 | 49 | 48 | |
| 24 | 0 | 1 | | 0 | 1 | | | 1 | 55 | 52 | 54 | |
| 25 | | | FLEA CHALLENGE | | | | | | | | | |
| 26 | 6 | 17 | | 9 | 20 | | | 13 | 56 | 55 | 56 | |

Legend
AV: Average
DOGS TREATED: As for Table 1
FLEA CHALLENGE: As for Table 2

TABLE 7

TICK COUNTS ON FIELD DOGS TREATED WITH THE COMPOSITION OF EXAMPLE 1 (AT COAST)

| DAY | LONG HAIR DOG LL | MM | NN | OO | AV | SHORT HAIR PP | QQ | RR | SS | AV |
|---|---|---|---|---|---|---|---|---|---|---|
| | a(c) | b | a(c) | a(c)(d) | | a(b)(c)(e) | a(b)(c) | a | a(b) | |
| −7 | — | 50 | B(30) | 4(45)(0) | | — | — | — | 28(0) | |
| −6 | 6(10) | — | — | — | 38 | 2(1)(4)(0) | 1(1)(5) | 20 | — | 16 |
| 0 | 9(13) | 65 | 6(28) | 2(60)(2) | 46 | 5(2)(3)(0) | 1(5)(14) | 22 | 58(1) | 28 |
| 0 | | | | | DOGS TREATED | | | | | |
| 1 | 3(9) | 40 | 0(20) | 0(37)(0) | 27 | 0(0)(4)(0) | 0(0)(8) | 7 | 26(0) | 11 |
| 6 | 5(2) | 15 | — | — | | 0(0)(1)(0) | 0 | — | 5(0) | |
| 7 | | | 1(13) | 0(21)(0) | 14 | | | 5 | — | 3 |
| 9 | — | 7 | — | — | | — | | | | |
| 10 | 1(1) | — | 1(14) | 1(4)(0) | | 0(0)(2)(0) | 0(2)(0) | 2 | 6(0) | |
| 14 | 1(3) | 5 | — | — | 6 | 0(0)(2)(0) | 0 | — | 13(0) | 4 |
| 15 | — | — | 0(2) | 1(3)(0) | | — | — | 5 | — | |
| 16 | — | 13 | — | — | | — | — | — | — | |
| 17 | 0 | — | 0(10) | 0(6)(0) | | 0(0)(1)(0) | 0 | 2 | 12(0) | |
| 21 | 0 | 9 | — | — | 7 | 0(0)(2)(0) | 1(0)(2) | — | 18(0) | 5 |
| 22 | — | — | 0(7) | 0(10)(0) | | — | — | 4 | — | |
| 24 | 1(0) | — | — | — | | 0(0)(2)(0) | 0(1)(2) | — | 24(0) | |
| 28 | 0 | 14 | 0(5) | 0(7)(0) | 8 | 0(0)(2)(0) | 0 | 4 | 22(0) | 9 |

Legend
(i) a(b)(c)(d)(e): a represents *Haemaphysalis leachi* ticks b represents *Rhipicephalus sanguineus* ticks c represents *Amblyomma hebraeum* ticks d represents *Goophilus decoloratus* ticks e represents *Ixodes pilosis* ticks
(ii) AV: Average
(iii) DOGS TREATED: As for Table 1

TABLE 8

FLEA COUNTS ON DOGS TREATED WITH THE COMPOSITION OF EXAMPLE 1 (AT COAST)

| WEEK | DAY | LONG HAIR DOG TT | UU | AV | SHORT HAIR VV | WW | XX | YY | AV |
|---|---|---|---|---|---|---|---|---|---|
| WEEK 1 | −7 | 20 | 10 | 15 | — | — | — | 20 | |
| | −6 | — | — | — | 60 | 10 | 22 | — | 28 |
| | 0 | 25 | 15 | 20 | 40 | 15 | 22 | 17 | 24 |
| | 0 | | | DOGS TREATED | | | | | |
| | 1 | 0 | 1 | 1 | 0 | 10 | 3 | 15 | 7 |
| WEEK 1 | 6 | — | 0 | — | 0 | 0 | — | 0 | |
| | 7 | 0 | — | 0 | — | — | 0 | — | 0 |
| | 10 | — | 0 | — | 0 | 0 | 0 | 8 | |
| WEEK 2 | 11 | 1 | — | — | — | — | — | — | |
| | 14 | 0 | 2 | 1 | 0 | 0 | — | 5 | 2 |
| | 15 | — | — | — | — | — | 0 | — | |
| WEEK 3 | 17 | — | 1 | — | 1 | 0 | 3 | 3 | |
| | 18 | 1 | — | — | — | — | — | — | |
| | 21 | 1 | 2 | 1 | 1 | 0 | — | 6 | 2 |
| | 22 | — | — | — | — | — | 1 | — | |
| WEEK 4 | 24 | — | 2 | — | 1 | 5 | — | 20 | |
| | 25 | 2 | — | — | — | — | — | — | |
| | 28 | 4 | 3 | 3 | 1 | 0 | 1 | 22 | 6 |

Legend
AV: Average
DOGS TREATED — As for Table 1

TABLE 9

TICK COUNTS ON DOGS TREATED WITH THE COMPOSITION OF EXAMPLE 1 (ON THE SOUTH AFRICAN HIGHVELD)

| DAY | DOG AF | DOG AG | DOG AH | DOG AI |
|---|---|---|---|---|
| 0−2 | 87 (50+) | — | 2 | |
| 0 | 117 (60+) | 6 | 2 | 4 |
| | DOGS TREATED | | | |
| 1 | 51 (50+) | 4 | 2 | 0 |
| 7 | 20 (20+) | 4 | 2 | 1 |
| 14 | 25 (20+) | 0 | 0 | 0 |
| 21 | 77 (30+) | 4 | 0 | 0 |
| 26 | 110 (30+) | 2 | 0 | 0 |

Legend
(i) (X): engorged larvae and nymphae
(ii) DOGS TREATED: As for Table 1

TABLE 10

FLEA COUNTS ON DOGS TREATED WITH THE COMPOSITION OF EXAMPLE 1 (ON THE SOUTH AFRICAN HIGVELD)

| DAY | DOG AB | DOG AC | DOG AD | DOG AE |
|---|---|---|---|---|
| −7 | nc | 31 | 17 | nc |
| −2 | nc | 50 | 15 | 65 |
| 0 | 23 | 74 | 23 | 100+ |
| | DOGS TREATED | | | |
| 1 | 0 | 1 | 0 | 0 |
| 7 | 4 | 1 | 0 | 0 |
| 14 | 13 | 7 | 1 | 5 |
| 21 | 15 | 21 | 1 | 14 |
| 26 | 25 | nc | 0 | nc |

TABLE 10-continued
FLEA COUNTS ON DOGS TREATED WITH THE
COMPOSITION OF EXAMPLE 1
(ON THE SOUTH AFRICAN HIGVELD)

| DAY | DOG AB | DOG AC | DOG AD | DOG AE |
|---|---|---|---|---|
| 29 | nc | 27 | nc | 26 |

Legend
(i) nc: no count
(ii) DOGS TREATED: As for Table 1.

Hence, the biological trials to determine formulation efficacy comprised two components - namely field trials (Tables 3, 4, 7, 8, 9, and 10) and controlled trials (Tables 1, 2, 5, and 6). The former (field trials) comprised choosing suitable naturally infested dogs and the latter controlled trials involved a number of dog housed in the Small Animal Unit (SAU) of the Kwanyanga Research Station located near East London in the Cap Province, Republic of South Africa. The regular tick and flea counts were carried out according to standard Kwanyanga procedures. In the controlled trials, the dogs were artificially infested with the stated numbers of ticks and fleas for two days prior to treatment with the pour-on formulations and at weekly intervals for the duration of the trial.

The field trials were carried out at the coast (East London) and on the South African Highveld (Pretoria area).

As mentioned hereinbefore, the pour-ons were applied along the backline of the dogs at the minimum recommended dose of 30 mg insectiside kg. However, the dosage range be can varied between 30 and 60 mg total insecticide/kg, irrespective of the dog size, viz small, medium or large.

The efficiency of the pour-on formulations against ticks and fleas on dogs under controlled conditions and in field trials is evident from the Tables. It can be seen that in general there is a rapid reduction in tick and flea numbers immediately after treatment and that these low levels are normally maintained for 1 to 3 weeks in the case of the formulations at Example 2 and 2-4 weeks in the case of the formulations of Example 1. In particular from Tables 1 and 2 it can be noted that, in respect of dogs treated with the compositions of Example 1, tick and flea numbers were reduced from an initial average of thirty-two and twenty-nine respectively to zero, by day one (ie the day after the composition of Example 1 was applied) in the case of fleas and by day eleven in the case of ticks. Very good control was maintained for thirty nine days despite weekly challenge and no further dog treatment.

From Tables 1 and 2 it can also be seen that, in respect of dogs treated with the composition of Example 2, tick and flea numbers were reduced from an initial average of thirty-four and thirty-nine respectively, to zero by day 1 in the case of fleas, and to four by day 11 in the case of ticks.

In field trials (Tables 3, 4, 7, 8, 9, and 10) comparable good results were achieved with the compositions of Examples 1 and 2 when applied to long and short haired dogs.

Generally in respect of fleas, an extremely high degree of control was maintained during the trials, and in general a very rapid reduction in flea population was obtained immediately after treatment. Some of the controlled trial dogs were re-treated after 28 days and a high degree of control was thereafter also maintained for a further four weeks.

The field trial results both at the coast and on the Highveld supported the results generated under controlled conditions. From the Tables it emerged that of Example 2 is that good results will be obtained by re-treating the dogs at regular intervals of two to three weeks with the formulations of Example 2, and at regular intervals of about four weeks with the formulations of Example 1.

The Applicant also believes that the insecticidal composition according to the invention will have the following advantages:

the insecticide can be selected so that it is substantially non-toxic when consumed by the animal (eg when the animal licks itself) to which it has been applied at the recommended dosage rate the animal looks neat after application of the composition as it does not leave an oily mark on the hair or skin of the animal; the non-systemic insecticide is effective biologically;

the composition after application dries quickly due to the volatility of the carrier;

the composition is applied easily;

the composition is cosmetically acceptable;

the composition is tolerable to the animal, eg is non-irritant and non-harmful to the animal.

While there is, as stated above, little or no run-off of insecticide on application, there is some spreading of the insecticide in the immediate vicinity of the spot or location of application on the pelt of the animal. This is due primarily to the low viscosity of the solvent. This spreading, the Applicant believes, attributes to the efficacy of the composition. Hence, the composition contains no substance which will interfere with or hinder this spreading, such as gel-forming or film-forming agents. The Applicant believes that, should an animal be treated with an insecticidal composition incorporating such gel- or film-forming agents, a visible bead or film of composition can be deposited on the animal, which is unsightly and could be cosmetically unacceptable to a user.

I claim:

1. A dog pour-on formulation for localized external application to dogs, which includes
   an insecticidally effective amount of a non-systemic compound which is tolerated by dogs and which is effective against insects selected from the group consisting of fleas and ticks; and
   a $C_1$-$C_4$ alcohol as carrier for the compound, with the proviso that the formulation contains no pyrethroid, no spreading oil, and no gel- or film-forming agent.

2. A formulation according to claim 1, which includes from 1 to 10% (m/v) of the non-systemic compound, the non-systemic compound comprising an organophosphorus compound selected from the group consisting of diazinon, tetrachlorvinphos, dursban and phosmet, and the alcohol comprising a monohydric aliphatic alcohol.

3. A formulation according to claim 2, wherein the organophosphorus compound is dursban, and wherein the alcohol is n-propanol.

4. A formulation according to claim 1, which is in unit dosage form.

5. A method of controlling, on a dog, insects selected from the group consisting of fleas and ticks, the method including applying locally and externally at intervals of from about 1 to about 4 weeks, an insecticidally effective volume of a pour-on formulation comprising a non-systemic compound which is tolerated by dogs and which is effective against said insects; and a $C_1$–$C_4$ alcohol as carrier for the compound, so that the compound is applied at an insecticidally effective rate and with no spreading oil being present in the formulation.

6. A method according to claim 5, wherein the application is effected by pouring the formulation along the back of the dog, and wherein the formulation includes from 1 to 10% (m/v) of the non-systemic compound, at least 90% (by volume) of the carrier, and no spreading oil and no gel-forming agent.

7. A method according to claim 5, wherein the non-systemic compound comprises an organophosphorus compound selected from the group consisting of diazinon, tetrachlorvinphos, dursban, and phosmet, and the carrier is a monohydric aliphatic alcohol.

8. A method according to claim 7, wherein the formulation includes as a further non-systemic compound a pyrethroid selected from the group consisting of permethrin, deltramethrin, tetramethrin, cypermethrin, and flumethrin.

9. A method according to claim 8, wherein the formulation comprises about 4% (m/v) dursban, about 4% (m/v) permethrin, and the balance to make up 100 volume units being n-propanol.

* * * * *